United States Patent
Yamamoto et al.

(10) Patent No.: US 7,786,324 B2
(45) Date of Patent: Aug. 31, 2010

(54) METHOD FOR PRODUCING BORAZINE COMPOUND

(75) Inventors: Tetsuya Yamamoto, Hyogo (JP); Takuya Kamiyama, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/845,322

(22) Filed: Aug. 27, 2007

(65) Prior Publication Data

US 2008/0045750 A1 Feb. 21, 2008

Related U.S. Application Data

(62) Division of application No. 11/346,545, filed on Feb. 2, 2006, now Pat. No. 7,692,043.

(30) Foreign Application Priority Data

| Feb. 3, 2005 | (JP) | ............... | 2005-028068 |
| Feb. 7, 2005 | (JP) | ............... | 2005-030598 |
| May 24, 2005 | (JP) | ............... | 2005-151501 |
| Aug. 24, 2005 | (JP) | ............... | 2005-242733 |

(51) Int. Cl.
*C07F 5/02* (2006.01)
(52) U.S. Cl. ...................................... 564/10
(58) Field of Classification Search ............ 568/3; 423/285, 290, 409; 564/10
See application file for complete search history.

(56) References Cited

U.S. PATENT DOCUMENTS

| 3,102,911 | A | | 9/1963 | Dorbaltz |
| 3,119,864 | A | | 1/1964 | Leffler .................. 260/551 |
| 3,255,245 | A | * | 6/1966 | Horn et al. ............... 564/10 |
| 4,150,097 | A | | 4/1979 | Hough et al. ............... 260/551 |
| 5,612,013 | A | | 3/1997 | Sneddon et al. |
| 2005/0177002 | A1 | | 8/2005 | Yamamoto et al. ............ 564/10 |

FOREIGN PATENT DOCUMENTS

| GB | 984907 | * | 3/1965 |
| JP | 2005112723 | * | 4/2005 |
| JP | 2005-179232 | | 7/2005 |

OTHER PUBLICATIONS

Framery et al., "Efficient Synthesis and NMR Data of N- or B-Substituted Borazines", Heteroatom Chemistry 11:218-225, 2000, XP008061913.
Meller, Gmelin Handbuch der Anorganischen Chemie Band 51, pp. 36-55, 72-83, 130-159, 1978.
Moon et al., "A Route to Boron Nitride Via Simply Prepared Borazine Precursor", Bull. Korean Chem. Soc. 19:222-226, 1998, XP008061843.
Muetterties, Boron Hydride Chemistry, pp. 241-272, 1975.
Schaeffer et al., "The Preparation of Trimethylamine-borine, N-Trimethylborazole and N-Dimethyl-Aminoborine", J. Am. Chem. Soc. 71:2143-2145, 1949, XP002372995.
Wideman et al., "Borazine, Polyborazylene, B-Vinylborazine, and Poly(B-Vinylborazine)", 32:232-242, 1998, XP008061852.
Wideman et al., "Convenient Procedures for the Laboratory Preparation of Borazine", Inorg. Chem. 34:1002-1003, 1995, XP-002372997.
Steinberg, Organic Chemistry vol. 2, pp. 221-231, 244-266, 1966.

* cited by examiner

*Primary Examiner*—Jafar Parsa
(74) *Attorney, Agent, or Firm*—Occhiuti Rohlicek & Tsao LLP

(57) ABSTRACT

In a synthesis of a borazine compound by a reaction of an alkali boron hydride represented by $ABH_4$ (A represents lithium atom, sodium atom or potassium atom) and an amine salt represented by $(RNH_3)_nX$ (R represents a hydrogen atom or an alkyl group, X represents a sulfate group or a halogen atom, and n is 1 or 2), or b) diborane ($B_2H_6$) and an amine represented by $RNH_2$ (R represents a hydrogen atom or an alkyl group), a water content of raw material is controlled below a prescribed value; mixed solvents containing solvents each having a prescribed boiling point are used as a solvent for reaction; or a raw material is gradually fed to a reactor in a reaction. Or, a borazine compound is subjected to distillation purification treatment and filtration treatment. By such a method, a high purity of borazine compound can be produced safely and in a high yield.

2 Claims, No Drawings

METHOD FOR PRODUCING BORAZINE COMPOUND

CROSS-REFERENCE TO RELATED APPLICATIONS

This application is a divisional of U.S. application Ser. No. 11/346,545, filed on Feb. 2, 2006, which claims priority to Japanese Patent Application No. 2005-242733, filed Aug. 24, 2005; Japanese Patent Application No. 2005-151501, filed May 24, 2005; Japanese Patent Application No. 2005-030598, filed Feb. 7, 2005 and Japanese Patent Application No. 2005-028068, filed Feb. 3, 2005, the content of which is hereby incorporated by reference in its entirety.

BACKGROUND OF THE INVENTION

1. Field of the Invention

The present invention relates to a method for producing borazine compounds. Borazine compounds are used to form, for example, an interlayer dielectric film for semiconductor, a barrier metal layer and an etching stopper layer.

2. Description of Related Art

With higher functionalization of information devices, design rule of LSI has been required to be finer year by year. In production of LSI with finer design rule, materials composing LSI should also have higher performance and fulfill function even on fine LSI.

For example, as for materials used for an interlayer dielectric film in LSI, high dielectric constant causes signal delay. In fine LSI, effects of the signal delay is particularly significant. Therefore, development of a new low dielectric material which can be used for an interlayer dielectric film has been needed. Also, it is necessary not only to have low dielectric constant but also superior characteristics such as humidity resistance, heat resistance, mechanical strength, etc. to be used as an interlayer dielectric film.

As a material to respond to these requirements, a compound having borazine ring backbone has been proposed (for example, see US Laid Open Patent No. 2002-58142). A compound having borazine ring backbone (borazine compound) has small molecular polarizability and thus a coated film formed provides low dielectric constant. Moreover, the coated film formed is superior in heat resistance.

As a borazine compound, N-alkylborazine in which a nitrogen atom constructing the borazine rings is bonded with an alkyl group. N-alkylborazine in itself is used for a raw material to form an interlayer dielectric film for semiconductor and the like. Further, N-alkylborazine is also used as an intermediate compound in producing other borazine compounds. For example, hexaalkylborazine is produced by substituting a hydrogen atom bonded to a boron atom in a borazine compound with an alkyl group.

As a technique for producing a borazine compound, 1) a technique reacting an alkali boron hydride (for example, sodium boron hydride ($NaBH_4$)) and an amine salt (for example, methylamine hydrochloride ($CH_3NH_3Cl$)) in a solvent; 2) a technique reacting diborane ($B_2H_6$) and an amine compound (for example, methylamine ($CH_3NH_2$)) in a solvent; are known.

BRIEF SUMMARY OF THE INVENTION

The present inventors have, after analyzing in detail borazine compounds obtained by the synthetic techniques, found that the borazine compounds contains various impurities, which cause lowering of a purity of the desired borazine compound. Specifically, in addition to a compound which is thought to be a decomposed matter of borazine compound (for example, amine and boric acid) and a boron ether compound which is formed by a trace component in a solvent, in a synthesis of a N-alkylborazine compound, N-alkylcycloborazane of a by-product can be contained as an impurity. In view of application to precision apparatus such as an interlayer dielectric film, a content of these compounds contained as impurities is desirably lowered to a level as low as possible. Further, formation of N-alkylcycloborazane as a by-product in a synthesis of a borazine compound arises another problem. Namely, as synthesis of a borazine compound proceeds, N-alkylcycloborazane having a sublimation property deposits in a cooling section of synthesis apparatus. Further progression of deposition of N-alkylcycloborazane could lead, in some instances, to blockage of a cooling section to make continuation of synthesis impossible. Furthermore, safety could be impaired due to rise of pressure in a synthesis apparatus. Even when the deposition is removed before blocking a cooling section, stoppage of synthesis is needed regularly, leading to lowering of synthesis efficiency. For a purpose of reference, structures of N-alkylborazine, boron ether compound and N-alkylcycloborazane are shown below:

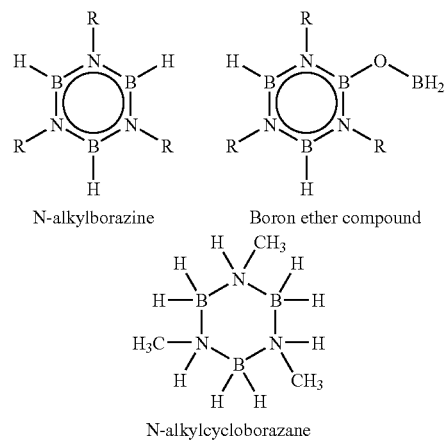

N-alkylborazine      Boron ether compound

N-alkylcycloborazane wherein R represents an alkyl group.

Further, the present inventors have found that hydrogen gas is formed accompanied to a reaction in these synthesis techniques, and sometimes a phenomenon happen to occur in which a large amount of hydrogen gas is formed in the reaction, and that various problems are caused by this phenomenon. For example, scaling up of the synthesis reaction increases an amount of hydrogen gas to be formed, and too much increase of an amount of hydrogen gas formed could lead to an impairment of sufficient assurance of safety in a production circumstances. Further, when such an embodiment is employed that distillation purification is carried out directly after completion of the reaction by a distillation purification equipment installed to a reactor, reaction solution is blown even to the distillate side together with the hydrogen gas spouted up, causing lowering in purification efficiency.

Thus, an object of the present invention is to provide a mean for producing a high purity of borazine compound safely and in a high yield.

According to an aspect of the present invention, a method for producing a borazine compound having a step to prepare a) an alkali boron hydride represented by $ABH_4$ (A represents a lithium atom, a sodium atom or a potassium atom) and an amine salt represented by $(RNH_3)_nX$ (R represents a hydrogen atom or an alkyl group, X represents a sulfate group or a halogen atom, and n is 1 or 2) with a water content not higher than 1% by mass, or b) diborane ($B_2H_6$) and an amine represented by $RNH_2$ (R represents a hydrogen atom or an alkyl group) with a water content not higher than 1% by mass, and a step to synthesize a borazine compound by reacting the alkali boron hydride and the amine salt, or the diborane and the amine in a solvent, is provided. By the method of the present aspect, a high purity of borazine compound with a lower content of decomposed matter can be produced in a high yield.

According to another aspect of the present invention, a method for producing a borazine compound having a step to prepare a) an alkali boron hydride represented by $ABH_4$ (A represents a lithium atom, a sodium atom or a potassium atom) and an amine salt represented by $(RNH_3)_nX$ (R represents a hydrogen atom or an alkyl group, X represents a sulfate group or a halogen atom, and n is 1 or 2), or b) diborane ($B_2H_6$) and an amine represented by $RNH_2$ (R represents a hydrogen atom or an alkyl group), and a step to synthesize a borazine compound by reacting the alkali boron hydride and the amine salt, or the diborane and the amine in mixed solvents containing a first solvent having a boiling point not lower than the boiling point of the borazine compound+50° C. and a second solvent having a boiling point not higher than the boiling point of the borazine compound+30° C., is provided.

According to further another aspect of the present invention, a method for producing a borazine compound having a step to prepare a) an alkali boron hydride represented by $ABH_4$ (A represents a lithium atom, a sodium atom or a potassium atom) and an amine salt represented by $(RNH_3)_nX$ (R represents a hydrogen atom or an alkyl group, X represents a sulfate group or a halogen atom, and n is 1, or 2), or b) diborane ($B_2H_6$) and an amine represented by $RNH_2$ (R represents a hydrogen atom or an alkyl group), and a step to synthesize a borazine compound by reacting the alkali boron hydride and the amine salt, or the diborane and the amine in a solvent by gradually feeding into a reactor at least one of i) the alkali boron hydride or the diborane, and ii) the amine salt or the amine, is provided. By the method of the present aspect, an amount of hydrogen gas formed in producing a borazine compound is controlled, and a borazine compound can be produced safely and in a high yield.

According to further another aspect of the present invention, a method for producing a borazine compound having a step to prepare a) an alkali boron hydride represented by $ABH_4$ (A represents a lithium atom, a sodium atom or a potassium atom) and an amine salt represented by $(RNH_3)_nX$ (R represents a hydrogen atom or an alkyl group, X represents a sulfate group or a halogen atom, and n is 1, or 2), or b) diborane ($B_2H_6$) and an amine represented by $RNH_2$ (R represents a hydrogen atom or an alkyl group), and a step to synthesize a borazine compound by reacting the alkali boron hydride and the amine salt, or the diborane and the amine in a solvent, while a solvent is fed to a cooling section of a synthesis apparatus, is provided. By the method of the present aspect, the problem that a deposition is formed in a cooling section of a synthesis apparatus in synthesizing a borazine compound is effectively suppressed, and a borazine compound can be produced safely and in a high yield.

According to further another aspect of the present invention, a method for producing a purified N-alkylborazine having a step to purify by distilling an N-alkylborazine and a step to remove a compound deposited in the N-alkylborazine by filtration. By the method of the present aspect, a purified N-alkylborazine with a high purity can be obtained.

According to further another aspect of the present invention, an N-alkylborazine containing an N-alkylcycloborazane and a boron ether compound in a total content not higher than 0.1% by mass is provided.

By these aspects, an N-alkylborazine containing a very low content of a boron ether compound can be obtained. As a result, characteristics of an interlayer dielectric film and the like produced using an N-alkylborazine can be improved.

DETAILED DESCRIPTION OF THE INVENTION

In an aspect, the present invention relates to a method for producing a borazine compound. In the method of the present invention, a borazine compound is synthesized by a reaction of an alkali boron hydride represented by $ABH_4$ (A represents a lithium atom, a sodium atom or a potassium atom) and an amine salt represented by $(RNH_3)_nX$ (R represents a hydrogen atom or an alkyl group, X represents a sulfate group or a halogen atom, and n is 1 or 2) (hereinafter, also referred to as "reaction 1"), or a reaction of diborane ($B_2H_6$) and an amine represented by $RNH_2$ (R represents a hydrogen atom or an alkyl group) (hereinafter, also referred to as "reaction 2"). Here, in the present application, "borazine" means borazine ($B_3N_3H_6$) in which none of boron atom nor nitrogen atom is bonded with an alkyl group, and "borazine compound" means a borazine derivative in which at least one of nitrogen atom is bonded with an alkyl group.

Hereinbelow, the method of the present invention will be explained in detail.

Firstly, raw materials necessary for the reaction are prepared. In the reaction 1, an alkali boron hydride represented by $ABH_4$ (A represents a lithium atom, a sodium atom or a potassium atom) and an amine salt represented by $(RNH_3)_nX$ (R represents a hydrogen atom or an alkyl group, X represents a sulfate group or a halogen atom, and n is 1 or 2) are prepared as raw materials.

In the alkali boron hydride ($ABH_4$), A represents a lithium atom, a sodium atom or a potassium atom. Examples of the alkali boron hydride include sodium boron hydride and lithium boron hydride.

In the amine salt ($(RNH_3)_nX$), R represents a hydrogen atom or an alkyl group; X represents a sulfate group or a halogen atom; and n is 2 when X is a sulfate group, and n is 1 when X is a halogen atom. Halogen atom is preferably a chlorine atom. When n is 2, R may be the same or different from each other. In view of yield in the synthesis reaction and easiness in handling, R is preferably an alkyl group being same to each other. The alkyl group may be straight chained, branched or cyclic. Number of carbon atom of the alkyl group is not especially limited, but preferably 1 to 8 atoms, more preferably 1 to 4 atoms, and furthermore preferably one atom. Specific examples of the alkyl group include, for example, methyl group, ethyl group, propyl group, isopropyl group, butyl group, isobutyl group, sec-butyl group, tert-butyl group, pentyl group, isopentyl group, neopentyl group, hexyl group, heptyl group, octyl group, nonyl group, decyl group, cyclopropyl group, cyclopentyl group and cyclohexyl group. An alkyl group other than these may be also used. Examples of the amine salt include ammonium chloride ($NH_4Cl$), monomethylamine hydrochloride ($CH_3NH_3Cl$), monoethylamine hydrochloride ($CH_3CH_2NH_3Cl$), monomethylamine hydrobromide ($CH_3NH_3Br$), monoethylamine hydrofluoride ($CH_3CH_2NH_3F$), ammonium sulfate (($NH_4)_2SO_4$) and monomethylamine sulfate (($CH_3NH_3)_2SO_4$).

On the other hand, in the reaction 2, as raw materials of the reaction, diborane ($B_2H_6$) and an amine represented by $RNH_2$ (R represents a hydrogen atom or an alkyl group) are prepared.

Diborane is a compound represented by the chemical formula "$B_2H_6$". Here, diborane may be a complexed one with tetrahydrofuran or the like. Further, regarding to the amine, R is same as explained for the amine salt in the paragraph for raw materials of the reaction 1, and hence explanation will be omitted here.

The raw materials to be used may be selected corresponding to a structure of a borazine compound to be synthesized. For example, when N-trimethylborazine in which N atoms constructing a borazine ring are bonded with methyl groups is produced, an amine salt or an amine wherein R is a methyl group, such as monomethylamine hydrochloride as an amine salt, and monomethylamine as an amine, may be used.

Method for obtaining raw materials is not especially limited. Each of the raw materials described above may be synthesized according to a known technique, or used by purchasing a commercial product.

In an aspect of the present invention, as a raw material for synthesizing a borazine compound, an amine salt (when a borazine compound is synthesized by the reaction 1) or an amine (when a borazine compound is synthesized by the reaction 2) with a low water content is used.

Specifically, in the present aspect, water content in the amine salt or the amine as a raw material is not higher than 1% by mass, preferably not higher than 0.1% by mass and more preferably not higher than 0.05% by mass. By synthesizing using the amine salt or the amine with such low water content, synthesis of a high purity of borazine compound becomes possible. Mechanism thereof is not clear, but it is speculated that decomposition of the synthesized borazine compound caused by mix-in of water is effectively inhibited. Further, when a borazine compound is synthesized by the reaction of diborane and an amine, if water content of the amine is high, diborane rapidly reacts with water contained in the amine to form boric acid. Contrary, according to the present aspect, occurrence of such problem can be also effectively suppressed. In this connection, as a value of water content in an amine salt or an amine as a raw material, a value measured by the method used in Examples described later will be employed. Further, from the above viewpoint, a water content of an amine salt or an amine is preferably as low as possible. The lower limit of the water content is not especially limited, but a water content of an amine salt or an amine for practical use is preferably not lower than 10 ppm by mass.

Route to obtain an amine salt or an amine with lower water content is not especially limited. When a commercial product of an amine salt or an amine with lower water content is available in the market, the product may be purchased and used, or after purchasing a commercial product with comparatively higher water content generally available in the market, the product may be used for synthesizing a borazine compound by personally reducing water content thereof.

Method for personally reducing water content of an amine salt or an amine is also not especially limited; a conventionally known knowledge in the field of chemical synthesis can be referred to, as appropriate. An example of the method for personally reducing water content of an amine salt or an amine includes, for example, heat drying, drying under reduced pressure and drying with desiccant (for example, silica gel and sodium sulfate). Among them, heat drying can be preferably employed. In this case, heating temperature is not especially limited, and a temperature as low as an amine salt or an amine is not decomposed and as high as drying time does not become too long, may be employed. Specifically, heating temperature in heat drying is preferably around 20 to 150° C. and more preferably around 60 to 100° C. Too low temperature in heat drying could require a long drying time. Contrary, too high temperature in heat drying could require a long cooling time for taking out.

The treatment for reducing water content of an amine salt or an amine by heat drying is preferably conducted under reduced pressure. In this case, specific pressure condition is not especially limited, but preferably around 0.0001 to 0.7 Pa and more preferably around 0.001 to 0.1 Pa. Too low pressure in reducing pressure could lead to sublimation of a borazine compound. Contrary, too high pressure in reducing pressure could require a long drying time.

In a preferable embodiment, water contents in other raw materials are also controlled at low levels. By such embodiment, decomposition of a borazine compound due to contact with moisture and lowering in purity accompanied thereto can be further suppressed.

Specifically, water content of an alkali boron hydride (when a borazine compound is synthesized by the reaction 1) or diborane (when a borazine compound is synthesized by the reaction 2) is preferably not higher than 1% by mass, more preferably not higher than 0.5% by mass and further more preferably not higher than 0.1% by mass. In this connection, as a value of water content of an alkali boron hydride or diborane, a value measured by the method used in an Example described later will be employed. Further, from the above viewpoint, a water content of an alkali boron hydride or diborane is preferably as low as possible. A lower limit of the water content is not especially limited, but a water content of an alkali boron hydride or diborane for practical use is preferably not lower than 10 ppm by mass.

Embodiments such as a route to obtain an alkali boron hydride or diborane with lower water content and a method for personally reducing water content are same as described above for an amine salt or an amine, hence explanation thereof will be omitted here.

In further another preferable embodiment, water content of a solvent used for synthesis (will be described later) is also controlled at a low level. By such embodiment, decomposition of a borazine compound due to contact with moisture and lowering in purity accompanied thereto can also be further suppressed.

Specifically water content of a solvent is preferably not higher than 1% by mass, more preferably not higher than 0.5% by mass and further more preferably not higher than 0.1% by mass. In this connection, as a value of water content of a solvent, a value measured by the method used in an Example described later will be employed. Further, from the above viewpoint, water content of a solvent is preferably as low as possible. A lower limit of the water content is not especially limited, but a water content of a solvent for practical use is preferably not lower than 10 ppm by mass.

Route to obtain a solvent with lower water content is not especially limited. When a commercial product of a solvent with lower water content is available in the market, the product may be purchased and used, or after purchasing a commercial product with comparatively higher water content generally available in the market, the product may be used for synthesizing a borazine compound by personally reducing water content thereof.

Method for personally reducing water content of a solvent is also not especially limited, and a conventionally known knowledge in the field of chemical synthesis can be referred to, as appropriate. An example of the method for personally reducing water content of a solvent includes, for example, such a method as distilling after adding desiccant.

Subsequently, a borazine compound is synthesized by reacting the raw materials prepared as described above in a solvent. In this case, a mixing ratio of an alkali boron hydride and an amine salt when a borazine compound is synthesized by the reaction 1 is not especially limited, but an amount of alkali boron hydride to be used is preferably 1.0 to 1.5 moles based on 1 mole of an amount of amine salt to be used. And also, a mixing ratio of diborane and an amine when a borazine compound is synthesized by the reaction 2 is not especially limited, but an amount of diborane to be used is preferably 1.0 to 1.2 moles based on 1 mole of an amount of amine to be used.

Solvent for synthesis is not especially limited, but includes, for example, tetrahydrofuran, monoethylene glycol dimethyl ether (monoglyme), diethylene glycol dimethyl ether (diglyme), triethylene glycol dimethyl ether (triglyme) and tetraethylene glycol dimethyl ether (tetraglyme).

In another aspect of the present invention, solvents of two or more kinds having different boiling points are used. Specifically, as solvents for synthesizing a borazine compound, a first solvent having a boiling point not lower than the boiling point of the borazine compound to be synthesized+50° C. and a second solvent having a boiling point not higher than the boiling point of the borazine compound to be synthesized+30° C. are used. In this connection, a boiling point of a borazine compound cannot be determined unambiguously, because it can be varied depending on a type of substituent thereof. For example, a boiling point of N,N',N''-trimethylborazine is 133° C./760 mmHg, and a boiling point of N,N',N''-triethylborazine is 184° C./760 mmHg.

A volatile component of the first solvent having a boiling point not lower than the boiling point of the borazine compound+50° C. liquefies comparatively rapidly on cooling in a cooling section of synthesis apparatus and returns to a heating section. And in the cooling section, a deposition represented by N-alkylcycloborazane is formed. On the other hand, a volatile component of the second solvent does not liquefy until reaching at a lower temperature. Thus, the second solvent liquefied by cooling passes through a site, where a deposition is formed, on a way to return to a heating section. On this occasion, the deposition is removed with the second solvent.

This mechanism can easily be understood if a cooling tube used in a laboratory scale synthesis is imagined. The first solvent liquefies at a lower part of the cooling tube and returns to a flask attached to the cooling tube. And in the lower part of the cooling tube, N-alkylcycloborazane deposits. On the other hand, the second solvent liquefies at the upper part of the cooling tube. On the way of the second solvent to return to a flask, the second solvent passes through a site, where N-alkylcycloborazane deposits, and N-alkylcycloborazane is washed away. However, the present invention is not limited to a laboratory scale of implementation. Even in an industrial scale of synthesis using a distillation column or the like, the present invention can be used.

As described above, in the present aspect, a first solvent having a boiling point not lower than the boiling point of the borazine compound+50° C. and a second solvent having a boiling point not higher than the boiling point of the borazine compound+30° C. are used, however, a third solvent may optionally be used. Further, as a first solvent and a second solvent, a plurality of solvents may be used.

The first solvent has a boiling point higher than the boiling point of the borazine compound to be synthesized by not lower than 50° C. The boiling point of a borazine compound means the boiling point of the borazine compound as a desired substance of the synthesis. When two or more kinds of borazine compounds are synthesized as desired substances, the boiling point of a borazine compound means a boiling point of a borazine compound having a higher boiling point. An upper limit of a boiling point of the first solvent is not especially limited, but since too high boiling point makes a separation by distillation purification difficult, preferably a solvent having a boiling point not higher than the boiling point of the borazine compound+150° C. is used.

A solvent included in the category of the first solvent is different depending on a boiling point of a borazine compound to be synthesized. Specific examples which can be used as the first solvent include, for example, tetrahydrofuran, monoethylene glycol dimethyl ether (monoglyme), diethylene glycol dimethyl ether (diglyme), triethylene glycol dimethyl ether (triglyme) and tetraethylene glycol dimethyl ether (tetraglyme).

The second solvent has a boiling point not higher than the boiling point of the borazine compound+30° C. Definition of the boiling point of a borazine compound is same as described above. A lower limit of a boiling point of the second solvent is not especially limited, but if the boiling point of the second solvent is close to a boiling point of a borazine compound as an objected substance, separation by distillation purification becomes difficult. Thus, the boiling point of the second solvent is preferably not lower than the boiling point of the borazine compound+10° C., or not higher than the boiling point of the borazine compound−10° C.

A solvent included in the category of the second solvent is also different depending on a boiling point of a borazine compound to be synthesized. Specific examples, which can be used as the second solvent, include, for example, ethers such as tetrahydrofuran, monoethylene glycol dimethyl ether (monoglyme), diethylene glycol dimethyl ether (diglyme), triethylene glycol dimethyl ether (triglyme) and tetraethylene glycol dimethyl ether (tetraglyme); aromatic hydrocarbons such as benzene, toluene, xylene, mesitylene, ethylbenzene, propylbenzene and isopropylbenzene; alicyclic hydrocarbons such as cyclohexane, tetralin and decalin.

In the present aspect, a mixing ratio of the first solvent and the second solvent is not especially limited, but for securing an effect to wash away the deposit with the second solvent, an amount of the second solvent to be used is preferably 0.1 to 2 times (by volume) based on 1 of an amount of the first solvent to be used.

The deposition formed in a cooling section of synthesis apparatus is removed with the second solvent, but more complete removal of the deposition may be intended. Even when deposition is compulsorily removed by stopping synthesis once, it is possible to prolong an interval of maintenance or reduce a maintenance work, because removal of the deposition has been done with the second solvent.

In further another aspect of the present invention, when a borazine compound is synthesized by reacting raw materials in a solvent, at least one of i) an alkali boron hydride (in the case of the reaction 1) or diborane (in the case of the reaction 2), and ii) an amine salt (in the case of the reaction 1) or an amine (in the case of the reaction 2) is gradually fed into a reactor.

Conventionally, in the reaction 1 and the reaction 2, a method for production had been employed in which reaction is progressed by charging both compounds as solid into a reactor then feeding a solvent thereto. However, in this method, due to presence of a whole amount of raw materials in the reaction system, under some conditions, a large amount of reactants could react instantaneously and a large amount of hydrogen gas could be instantaneously generated.

Therefore, in the present aspect, to prevent a large amount of hydrogen gas to be generated by a reaction, at least one of i) an alkali boron hydride (in the case of the reaction 1) or diborane (in the case of the reaction 2), and ii) an amine salt (in the case of the reaction 1) or an amine (in the case of the reaction 2) is gradually fed into a reactor. By this method, an instantaneous generation of a large amount of hydrogen gas is prevented. Hereinbelow, the reaction 1 will be specifically explained as an example, but the reaction 2 is also similar thereto.

As an embodiment to feed an alkali boron hydride and an amine salt into a reactor, the following three embodiments are exemplified. Firstly, an embodiment, in which a whole amount of an alkali boron hydride is charged into a reactor, then an amine salt is gradually fed into the reactor, is exemplified (a first embodiment). Secondly, an embodiment, in which a whole amount of an amine salt is charged into a reactor, then an alkali boron hydride is gradually fed into the reactor, is exemplified (a second embodiment). Thirdly, an embodiment, in which both of an alkali boron hydride and an amine salt are gradually fed into the reactor, is exemplified (a third embodiment).

In any embodiment, an instantaneous generation of a large amount of hydrogen gas is prevented, and various effects can be obtained. For example, since an amount of hydrogen gas to be generated can be controlled even when reaction is scaled up, a high safety is ensured. Further, when an embodiment is employed, in which distillation purification is carried out directly after completion of reaction by fitting a distillation purification equipment to a reactor, a phenomenon, that a reaction solution is blown to a distillate side together with hydrogen gas spouted out to lower purification efficiency, can be suppressed.

In the present aspect, an embodiment to feed a solvent in synthesizing a borazine compound is not especially limited. In the first embodiment, an amine salt is fed into a reactor charged with a whole amount of an alkali boron hydride, and a solvent may be fed into a reactor charged with an alkali boron hydride before feeding the amine salt. A solvent may be fed into a reactor in advance, and a solvent may be fed together with feed of an amine salt. Further, when a solvent is fed together with feed of an amine salt into a reactor, the amine salt may be fed after dissolving or dispersing the amine salt in a solvent, or charged separately into a reactor.

In the second embodiment, an alkali boron hydride is fed into a reactor charged with a whole amount of an amine salt, and a mode to feed a solvent is not especially limited similarly as in the first embodiment.

Also, in the third embodiment, a mode to feed a solvent is not especially limited. A solution composed of an alkali boron hydride and a solvent and a solution composed of an amine salt and a solvent may be prepared in advance then fed into a reactor. Only one of an alkali boron hydride and an amine salt is mixed with a solvent, and the other may be fed into a reactor as a solid. A solvent is fed into a reactor in advance, after that, an alkali boron hydride and an amine salt may be fed thereto.

In the present aspect, "gradually fed" is that a prescribed amount of component is fed in small portions instead of feeding in one portion. Feeding time may be determined corresponding to reaction scale and kind of compound to be used. For example, feeding is carried out over 0.5 to 5 hours. Feeding of raw materials into a reactor may be continuously or intermittently. If an amount to be fed can be determined by an empirical rule or an experiment, feeding may be controlled so that total amount to be fed becomes the prescribed amount.

Further, feeding of a solvent may be done automatically or manually. For example, when production is carried out in a laboratory scale, a solvent may be fed, as appropriate, while an amount of deposition is checked with eyes.

Temperature of a reaction solution in a reaction (the reaction 1 or the reaction 2) (hereinafter, also simply referred to as "reaction temperature") is not especially limited. Reaction temperature is preferably 20 to 250° C., more preferably 50 to 240° C., further preferably 50 to 220° C., further more preferably 70 to 150° C., still further more preferably 80 to 130° C. and yet further more preferably 100 to 120° C. When reaction is carried out at a temperature in the range, an amount of hydrogen gas to be generated can be easily controlled. Reaction temperature can be measured using a temperature sensor such as a K type thermo couple.

In this connection, "reaction temperature" means a temperature when a reaction (the reaction 1 or the reaction 2) proceeds. When an alkali boron hydride and an alkylamine salt are reacted (in the case of the reaction 1), N-alkylborazine is thought finally synthesized via an intermediate. In this case, "reaction temperature" does not mean a temperature throughout the whole reaction, but a temperature when reaction of an alkali boron hydride and an alkylamine salt proceeds.

Reaction temperature may be not constant, but varied during the reaction. For example, reaction temperature is controlled at a lower level in an initial stage of reaction to prevent N-alkylcycloborazane from converting to N-alkylborazine. And after most part of raw materials converted to N-alkylcycloborazane, reaction temperature is raised up to complete a synthesis of N-alkylborazine. Thus, when an embodiment is employed, in which after substantially completing the reaction of an alkali boron hydride and an alkylamine salt, a temperature of reaction solution is raised up to mature the reaction, the temperature until the reaction of an alkali boron hydride and an alkylamine salt is substantially completed corresponds to "reaction temperature".

A mechanism that an amount of hydrogen gas to be generated can be controlled by controlling reaction temperature is not clear, but it is presumed that a reaction in which N-alkylcycloborazane is converted to N-alkylborazine proceeds at a comparatively high temperature. Namely, in the synthesis of N-alkylborazine, N-alkylborazine is presumed to be formed by a mechanism that N-alkylcycloborazane having a general structure represented by the formula below is formed in first as an intermediate, then hydrogen ($3H_2$) is removed from N-alkylcycloborazane. And this reaction is thought to proceed at a comparatively high temperature. For this reason, by controlling reaction temperature in the above-described temperature range, most part of the reactant can be once stopped at a stage of N-alkylcycloborazane, thus preventing an instantaneous formation of a large amount of hydrogen gas. In this connection, the mechanism is a mere presumption, a technical scope of the present invention is by no means limited by the mechanism.

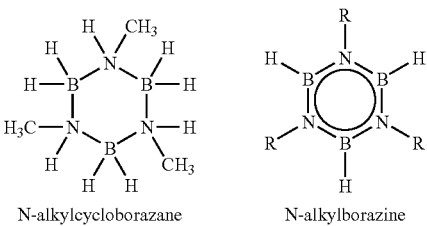

N-alkylcycloborazane      N-alkylborazine

On another aspect of the present invention, for a purpose to remove deposition formed in the cooling section of synthesis apparatus, a solvent is fed to the cooling section of synthesis apparatus in the synthesis. In the viewpoint that deposition is washed away with a solvent, the present aspect is similar to the aspect using mixed solvents described above. In the present aspect, deposition is washed away by a solvent fed to the cooling section of synthesis apparatus instead of using a solvent cooled and liquefied.

Specifically, in the synthesis, a solvent is fed to the cooling section of synthesis apparatus where deposition is accumulated. By feeding a solvent to a site where deposition is accumulated, accumulation of deposition in the cooling section is prevented. A solvent to be fed may be the same to the solvent used for synthesis of a borazine compound, or a different solvent may be used. As a solvent to be fed, those compounds exemplified above as a solvent to be used for synthesis can be similarly used.

An amount of a solvent to be fed differs depending on a structure of synthesis apparatus and scale of synthesis, and hence it is difficult to be unambiguously specified. Corresponding to a synthesis apparatus to be used, a sufficient amount of a solvent to remove deposition is preferably fed. However, since too large amount of a solvent to be fed leads to increase in cost of chemicals and scale-up of a production apparatus, an amount to be fed is preferably small.

Method for feeding a solvent is not especially limited as long as deposition can be removed. For example, a solvent feeding apparatus is installed above the cooling section of synthesis apparatus, so that necessary amount of a solvent and necessary timing of feeding can be controlled.

Feeding of a solvent may be continuous or intermittent. Further, feeding of a solvent may be automatic or manual. For example, when production is carried out in a laboratory scale, a solvent is fed, as appropriate, while an amount of deposition is checked with eyes.

By feeding a solvent, deposition formed in the cooling section of synthesis apparatus is removed, but more complete removal of the deposition may be intended. Even when deposition is compulsorily removed by stopping the synthesis once, it is possible to prolong an interval of maintenance or reduce a maintenance work, because removal of the deposition has been done with a solvent fed.

A borazine compound is a compound represented by the following formula.

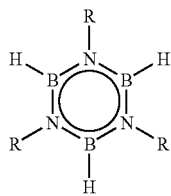

Wherein, R is the same as described for an amine salt in the paragraph for raw material of reaction 1, hence explanation is omitted here. An example of the borazine compound include, for example, borazine, N,N',N"-trimethylborazine, N,N',N"-triethylborazine, N,N',N"-tri(n-propyl)borazine, N,N',N"-tri(iso-propyl)borazine, N,N',N"-tri(n-butyl)borazine, N,N',N"-tri(sec-butyl)borazine, N,N',N"-tri(iso-butyl)borazine, N,N',N"-tri(tert-butyl)borazine, N,N',N"-tri(1-methylbutyl)borazine, N,N',N"-tri(2-methylbutyl)borazine, N,N',N"-tri(neo-pentyl)borazine, N,N',N"-tri(1,2-dimethylpropyl)borazine, N,N',N"-tri(1-ethylpropyl)borazine, N,N',N"-tri(n-hexyl)borazine, N,N',N"-tricyclohexylborazine, N,N'-dimethyl-N"-ethylborazine, N,N'-diethyl-N"-methylborazine, and N,N'-dimethyl-N"-propylborazine. In this connection, in view of stability such as water resistance of a borazine compound to be produced, a borazine compound is preferably N-alkylborazine.

A borazine compound synthesized can be purified, if necessary. As a method for purifying a borazine compound, for example, distillation purification is used. Distillation purification is a purification method to separate impurities through a work in which a liquid is heated to generate a gas and the gas is liquefied by cooling. Prior to the distillation purification, a treatment, which is general in the field of an organic synthesis, may be carried out. For example, a reaction solution is filtered and concentrated using an evaporator.

Size and type of the distillation purification equipment may be decided corresponding to circumstances and scale. For example, when a large amount of borazine compound is treated, an industrial scale of distillation column can be used. When a small amount of borazine compound is treated, distillation purification using a distillation tube can be used. For example, as a specific example of the distillation equipment for treating a small amount of borazine compound, a distillation equipment of a three-necked flask equipped with a Liebig condenser using a Claisen type connecting tube can be used. However, the technical scope of the present invention is by no means limited to an embodiment using such distillation equipment.

Distillation condition is not especially limited. Corresponding to a desired borazine compound, a technique such as an atmospheric distillation and a reduced pressure distillation may be selected. Temperature and pressure in the distillation are also not especially limited, but distillation temperature is preferably 130 to 180° C., and more preferably 140 to 160° C. Distillation pressure is preferably 0.6 kPa to 1.0 kPa, and more preferably 0.8 kPa to 1.0 kPa.

Distillation purification may be carried out optionally two or more times. Impurities are reduced to a suitable level by performing the distillation purification two or more times or using a multistage distillation column.

Preferably, even in a distillation purification step, a solvent is fed to a cooling section of distillation purification equipment. By feeding a solvent, formation of deposition in a cooling section can be suppressed even in the distillation purification step similarly as in a synthesis step. By this, even in the distillation purification equipment, blockage of the cooling section can be prevented, and purification efficiency can be improved. Embodiment for feeding a solvent in the distillation purification step is not especially limited, and the embodiment for feeding a solvent in a synthesis step described above can be similarly employed.

Further another aspect of the present invention relates to a technique for preventing contamination of impurities (in particular, an N-alkylcycloborazane and a boron ether compound) into a product when an N-alkylborazine is produced. Specifically, an N-alkylborazine is subjected to distillation purification, followed by removal of compounds deposited in the N-alkylborazine by filtration.

Route to obtain a N-alkylborazine to be purified in the present aspect is not especially limited. A high purity of N-alkylborazine may be produced by purchasing an N-alkylborazine available in the market, and purifying the N-alkylborazine. Alternatively, an N-alkylborazine may be obtained by synthesis. Since a technique to obtain an N-alkylborazine by synthesis is same as described above, explanation thereof is omitted here.

After an N-alkylborazine is obtained, the N-alkylborazine is purified to remove an N-alkylcycloborazane and/or a boron ether compound contained in the N-alkylborazine. Although a path of N-alkylcycloborazane formation is not clear, N-alkylcycloborazane is thought to be an intermediate to N-alkylborazine formation as described above. N-alkylborazine is formed by dehydrogenation of N-alkylcycloborazane, but a part of N-alkylcycloborazane is thought to remain. Further, by a minor component in raw materials, boron ether compound is formed. However, since this is s presumed mechanism, the technical scope of the present invention is by no means limited by N-alkylcycloborazane or boron ether compound formed by the mechanism.

As a method for producing purified N-alkylborazine, a combination of distillation purification and filtration is preferable. When a common purification method is used, sometimes concentrations of a N-alkylcycloborazane and a boron ether compound cannot be decreased to an acceptable level for use for semiconductor materials. However, by combining distillation purification and filtration as in the present aspect, an N-alkylcycloborazane and a boron ether compound can be removed to very low concentrations.

In a purification step, firstly N-alkylborazine is purified by distillation. Since specific embodiment of the distillation purification is the same as described above, explanation thereof is omitted here.

When an N-alkylcycloborazane and/or a boron ether compound is deposited in N-alkylborazine, an N-alkylcycloborazane and/or a boron ether compound deposited in N-alkylborazine is removed by filtration. Deposition of an N-alkylcycloborazane and/or a boron ether compound is formed when distillate is cooled down in a distillation purification step. If necessary, a process to cool distillate containing N-alkylcycloborazane may be specially added. When one of an N-alkylcycloborazane or a boron ether compound deposits, the compound deposited is removed by filtration. Both compounds may be removed by filtration. Though amounts of an N-alkylcycloborazane and/or a boron ether compound to be removed by filtration has a limitation, a purified N-alkylborazine having very low content of an N-alkylcycloborazane and/or a boron ether compound can be obtained by depositing a N-alkylcycloborazane and/or a boron ether compound in N-alkylborazine and removing them by filtration.

Filtration condition is not especially limited. Corresponding to circumstances and scale, a technique such as atmospheric filtration, pressure filtration and reduced pressure filtration may be selected. A kind of filter paper is also not limited. And corresponding to circumstances and scale, filter paper, filter plate, cartridge filter, and the like may be used. Further, a material of filter paper is also not limited, but in view of reactivity of a borazine compound to be synthesized, for example, filter paper made of polytetrafluoroethylene (PTFE) or glass fiber is preferably used. Pore size of filtration material may be determined corresponding to amount and size of deposition. Pore size of filtration material may be made smaller stepwise. Pore size of filtration material is preferably 0.8 to 0.05 μm, and more preferably 0.5 to 0.05 μm.

In purified N-alkylborazine provided by the present aspect, total content of an N-alkylcycloborazane and a boron ether compound is preferably not higher than 0.1% by mass, and more preferably not higher than 0.01% by mass. In this connection, when two or more kinds of N-alkylcycloborazane or boron ether compound are contained, "content" means the total including all of them. Content of a N-alkylcycloborazane is preferably not higher than 0.05% by mass, and more preferably not higher than 0.005% by mass. Also, content of a boron ether compound is preferably not higher than 0.05% by mass, and more preferably not higher than 0.005% by mass. The lower a content of a N-alkylcycloborazane and a boron ether compound in purified N-alkylborazine is, the more the purified N-alkylborazine is suitable to an application requiring a high purity such as an interlayer dielectric film for semiconductor.

Contents of an N-alkylcycloborazane and a boron ether compound in purified N-alkylborazine can be calculated using a known analyzer such as a gas chromatography. In this case, when a significant difference is seen among the values measured by different analyzers, a value obtained using the measuring method described in Examples is content in the present invention.

If a preferable purified N-alkylborazine is specified from the viewpoint of purity, a purified N-alkylborazine obtained by distillation purification and filtration has a purity of preferably not lower than 99.9% by mass, more preferably not lower than 99.99% by mass and further more preferably not lower than 99.999% by mass. According to the present aspect, such a high purity of purified N-alkylborazine can be produced, and by using the purified N-alkylborazine with a high purity, quality of products such as semiconductor devices can be improved.

Several aspects of the present invention described above can be used in combination. For example, in a synthesis reaction of a borazine compound, mixed solvents of the first solvent and the second solvent are used. And in a synthesis, the mixed solvents are fed to a cooling section of synthesis apparatus. By such way, formation of deposition in a cooling section of synthesis apparatus can be effectively suppressed.

In a more preferably embodiment, following the synthesis step, distillation purification step is carried out. In further more preferable embodiment, in the distillation purification step, the mixed solvents of the first solvent and the second solvent are fed in a cooling section of the distillation purification equipment. According to such an embodiment, formation of deposition in a cooling section is suppressed even in the distillation purification step, a borazine compound can be produced extremely safely and in a high yield.

Further, all of the aspects of the present invention may be used in combination. Namely, a borazine compound may be produced by a method for production having a step to prepare a) an alkali boron hydride represented by $ABH_4$ (A represents a lithium atom, a sodium atom or a potassium atom) and an amine salt represented by $(RNH_3)_nX$ (R represents a hydrogen atom or an alkyl group, X represents a sulfate group or a halogen atom, and n is 1 or 2) with a water content not higher than 1% by mass, or b) diborane ($B_2H_6$) and an amine represented by $RNH_2$ (R represents a hydrogen atom or an alkyl group) with a water content not higher than 1% by mass, a step to prepare mixed solvents containing a first solvent having a boiling point not lower than the boiling point of the borazine compound+50° C. and a second solvent having a boiling point not higher than the boiling point of the borazine compound+30° C., a step to synthesize a borazine compound by reacting the alkali boron hydride and the amine salt, or the diborane and the amine in the mixed solvents by gradually feeding into a reactor at least one of i) the alkali boron hydride or the diborane, and ii) the amine salt or the amine, a step to purify by distilling the synthesized borazine compound, and a step to remove a compound deposited in the borazine compound by filtration. According to such an aspect, a high purity of boazine compound can be produced safely and in a high yield.

In this connection, without any limitation to the combination described above, an aspect, in which each aspect of the present invention is optionally selected and combined, can also similarly be employed.

Use of a borazine compound is not especially limited, but the compound can be used to form a low dielectric constant film such as an interlayer dielectric film for semiconductor, a barrier metal layer and an etch stopper layer. In such case, a borazine compound may be used or a compound derived from a borazine compound by modification may be used. A polymer obtained by polymerizing a borazine compound or a borazine compound derivative may be used as a raw material for an interlayer dielectric film for semiconductor, a barrier metal layer or an etch stopper layer.

A polymer can be formed with a compound having a borazine ring skeleton as a monomer. Polymerization method and polymerization mode are not especially limited. Polymerization method is selected depending on a functional group bonded to a borazine ring. For example, when an amino group is bonded, a polymer can be synthesized by condensation polymerization. When a vinyl group or a functional group containing a vinyl group is bonded to a borazine ring, a polymer can be formed by radical polymerization using a polymerization initiator. A polymer may be a homopolymer, or a copolymer containing two or more monomer units. Type of copolymer may be any of a random copolymer, a block copolymer, a graft copolymer, and the like. By using a monomer having three or more functional groups which can form a bond with other monomer, a polymer in which monomers are bonded together like a network can be obtained.

Next, a method for forming an interlayer dielectric film for semiconductor, a barrier metal layer or an etch stopper layer will be explained. In this connection, in the following description, "a borazine compound", "a borazine compound derivative" and "a polymer originated with them" are referred to as "a borazine-ring-containing compound".

To form an interlayer dielectric film for semiconductor, a barrier metal layer or an etch stopper layer using a borazine-ring-containing compound, a technique to form a coating film by preparing a composition in a solution state or a slurry state containing the borazine-ring-containing compound, and coating this composition. A solvent used in such a case for dissolving or dispersing the borazine-ring-containing compound is not especially limited as long as the solvent can dissolve or disperse the borazine-ring-containing compound or other component to be added, if necessary. As the solvent, for example, alcohols such as ethylene glycol and ethylene glycol monomethyl ether; aromatic hydrocarbons such as toluene, benzene and xylene; hydrocarbons such as hexane, heptane and octane; tetrahydrofurane; diglyme; and tetraglyme, are used. These solvents may be used alone or in combination of two or more kinds. When film formation is performed using spin coating, diglyme is preferably used. By using diglyme or a derivative thereof as a solvent, a uniformity of a film to be produced is improved, and clouding of a film can be prevented. An amount of a solvent to be used for dissolving or dispersing the borazine-ring-containing compound is not especially limited, and may be determined corresponding to a production means for producing a low dielectric constant material. For example, when film formation is performed using spin coating, a kind and an amount of a solvent may be determined so that a viscosity becomes suitable for spin coating.

A composition containing the borazine-ring-containing compound is provided to a desired site, dried and solidified. For example, to form an interlayer dielectric film for semiconductor, the composition may be coated on a substrate by spin coating, and dried. When a film having a desired thickness cannot be obtained in one coating and drying, coating and drying may be repeated until a desired thickness is obtained. Film forming conditions such as number of revolutions of spin coater, drying temperature and drying time are not especially limited.

Coating on a substrate may be performed using a technique other than the spin coating. For example, spray coating and dip coating can be used.

After that, a coating film is dried. Drying temperature of a coating film is usually around 100 to 250° C. The "drying temperature" here means the highest temperature while drying treatment is carried out. For example, when a drying temperature is raised slowly, maintained at 10° C. for 30 min., and followed by cooling, a drying temperature is 100° C. Drying temperature can be measured using a thermo couple. Drying time for coating film is not especially limited, but may be determined, as appropriate, in consideration of characteristics such as dielectric constant and moisture resistance of a low dielectric constant material to be obtained.

EXAMPLES

Hereinbelow, embodiments of the present invention will be explained in detail using Examples and Comparative Examples, however, technical scope of the present invention is by no means limited to the following embodiments.

In the following Example 1 and Comparative Example 1, water contents of an amine salt and an alkali boron hydride as raw materials, as well as solvents were measured by the following techniques.

Namely, water contents of an amine salt and solvents were measured using the Karl Fischer AQ-7 (from Hiranuma Sangyo Co., Ltd.). In this case, Aqualyte RS as generator electrolyte and Aqualyte CN as counter electrolyte were used.

And water content of an alkali boron hydride was measured using the Karl Fischer CA-100 (from Mitsubishi Chemical Corp.). In this case, Aquamicron AX as generation liquid and Aquamicron CXU as counter electrode liquid were used.

Further, purity of a borazine compound was measured using a gas chromatography. Measuring conditions were as follows.

Equipment: GC-14B from Shimadzu Corp.
Column: Ultra Alloy (8H) from Hitachi Science Systems Ltd.
Carrier gas: Nitrogen
Flow rate of carrier gas: 3.0 mL/min.
Sample injection temperature: 300° C.
Detector temperature: 300° C.
Sample injection amount: 0.2 µL
Column temperature: 50° C. (5 min.)→raising temperature to 250° C. at a temperature raising rate of 20° C./min.→raising temperature to 300° C. at a temperature raising rate of 10° C./min.→300° C. (10 min.)

Example 1

Firstly, as an amine salt of raw material of reaction, methylamine hydrochloride was prepared. Then, this methylamine hydrochloride was subjected to heat drying under reduced pressure by standing under the atmosphere of 80° C., 0.07 MPa for 12 hours.

Similarly, as an alkali boron hydride of another raw material of reaction, sodium boron hydride was prepared. This sodium boron hydride was subjected to drying under reduced pressure by standing in the atmosphere of 25° C., 0.07 MPa for 12 hours.

On the other hand, as a solvent, triglyme was prepared. And by adding Molecular Sieve 3A (from Tomoe Engineering Co., Ltd.), this triglyme was dried.

Into a reactor equipped with a condenser, methylamine hydrochloride dried as described above (33.5 g; water content=200 ppm by mass) and triglyme dried as described above (98.6 g; water content=130 ppm by mass) were charged with nitrogen purge, then temperature of the reaction system was raised to 100° C.

On the other hand, sodium boron hydride dried as described above (21.0 g; water content=300 ppm by mass) was prepared, then added into triglyme dried as described above (88.7 g; water content=130 ppm by mass) prepared separately, to prepare a slurry.

The slurry of sodium boron hydride prepared as described above was slowly added over 1 hour to the reactor raised to 100° C. as described above.

After completion of addition of the slurry, the reaction system was raised to 200° C. over 2 hours, and further matured at 200° C. for 2 hours to synthesize N,N',N"-trimethylborazine.

The N,N',N"-trimethylborazine thus obtained was distilled at 150 to 220° C. to obtain 15.4 g of purified N,N',N"-trimethylborazine. Purity of the purified N,N',N"-trimethylborazine obtained was measured and found to be 99.8% by mass.

Comparative Example 1-1

Into a reactor equipped with a condenser, methylamine hydrochloride not dried (33.5 g; water content 1.3% by mass) and triglyme not dried (98.6 g; water content=2.0% by mass) were charged with nitrogen purge, then temperature of the reaction system was raised to 100° C.

On the other hand, sodium boron hydride not dried (21.0 g; water content=2.0% by mass) was prepared, then added into triglyme not dried (88.7 g; water content=2.0% by mass) prepared separately, to prepare a slurry.

The slurry of sodium boron hydride prepared as described above was slowly added over 1 hour to the reactor raised to 100° C. as described above.

After completion of addition of the slurry, the reaction system was raised to 200° C. over 2 hours, and further matured at 200° C. for 2 hours to synthesize N,N',N"-trimethylborazine.

The N,N',N"-trimethylborazine thus obtained was distilled at 150 to 220° C. to obtain 1.5 g of purified N,N',N"-trimethylborazine. Purity of the purified N,N',N"-trimethylborazine obtained was measured and found to be 93.5% by mass.

Comparative Example 1-2

Into a reactor equipped with a condenser, methylamine hydrochloride not dried (33.5 g; water content=2.0% by mass) and triglyme dried as described above (98.6 g; water content=250 ppm by mass) were charged with nitrogen purge, then temperature of the reaction system was raised to 100° C.

On the other hand, sodium boron hydride dried as described above (21.0 g; water content=400 ppm by mass) was prepared, then added into triglyme dried as described above (88.7 g; water content=250 ppm by mass) prepared separately, to prepare a slurry.

The slurry of sodium boron hydride prepared as described above was slowly added over 1 hour to the reactor raised to 100° C. as described above.

After completion of addition of the slurry, the reaction system was raised to 200° C. over 2 hours, and further matured at 200° C. for 2 hours to synthesize N,N',N"-trimethylborazine.

The N,N',N"-trimethylborazine thus obtained was distilled at 150 to 220° C. to obtain 8.7 g of purified N,N',N"-trimethylborazine. Purity of the purified N,N',N"-trimethylborazine obtained was measured and found to be 97.4% by mass.

From the results of Example 1 and Comparative Examples 1-1 and 1-2, it is shown that by controlling water content of an amine salt as a raw material of borazine compound at a low level, purity and yield of borazine compound to be synthesized can be improved. Further, it is also shown that by controlling water contents of an alkali boron hydrate as a raw material of borazine compound and a solvent used for synthesis at a low level, purity and yield of borazine compound to be synthesized can be further more improved.

Example 2-1

Into a 4 L reactor equipped with a cooling tube, methylamine hydrochloride (335 g) as an amine salt, tetraglyme (boiling point: 275° C.) (500 g) as a first solvent, and diglyme (boiling point: 162° C.) (500 g) as a second solvent were charged, then temperature of the reaction system was raised to 100° C.

On the other hand, sodium boron hydride (210 g) as an alkali boron hydride was prepared, then added into tetraglyme (1,000 g) prepared separately, to prepare a slurry.

The slurry of sodium boron hydride prepared as described above was slowly added over 90 min. to the reactor raised to 100° C. as described above.

After completion of addition of the slurry, the reaction system was raised to 200° C. over 30 min., and further matured at 200° C. for 2 hours to proceed a synthesis reaction of N,N',N"-trimethylborazine.

During raising temperature and maturing, formation of deposition and blockage of the cooling tube were observed by eyes, and it was found that the cooling tube was not blocked up though formation of the deposition was observed a little.

Example 2-2

Into a 4 L reactor equipped with a cooling tube having a solvent dropping device connected to the upper part thereof, methylamine hydrochloride (335 g) as an amine salt, triglyme (boiling point: 216° C.) (1,000 g) as a solvent were charged, then temperature of the reaction system was raised to 100° C.

On the other hand, sodium boron hydride (210 g) as an alkali boron hydride was prepared, then added into triglyme (1,000 g) prepared separately, to prepare a slurry.

The slurry of sodium boron hydride prepared as described above was slowly added over 90 min. to the reactor raised to 100° C. as described above.

After completion of addition of the slurry, the reaction system was raised to 200° C. over 30 min., and further matured at 200° C. for 2 hours to proceed a synthesis reaction of N,N',N"-trimethylborazine.

In this case, 20 g each of triglyme was dropped from the solvent dropping device 3 times in total during a period from completion of addition of the slurry until completion of raising temperature of the reaction system.

During raising temperature and maturing, formation of deposition and blockage of the cooling tube were observed by eyes, and it was found that though formation of the deposition was observed a little, this deposition was washed away by the dropped triglyme and the cooling tube was not blocked up.

Comparative Example 2

Into a 4 L reactor equipped with a cooling tube, methylamine hydrochloride (335 g) as an amine salt, and tetraglyme (boiling point: 275° C.) (1,000 g) were charged, then temperature of the reaction system was raised to 100° C.

On the other hand, sodium boron hydride (210 g) as an alkali boron hydride was prepared, then added into tetraglyme (1,000 g) prepared separately, to prepare a slurry.

The slurry of sodium boron hydride prepared as described above was slowly added over 90 min. to the reactor raised to 100° C. as described above.

After completion of addition of the slurry, the reaction system was raised to 200° C., and further matured at 200° C. to proceed a synthesis reaction of N,N',N''-trimethylborazine.

However, during the maturation, a deposition was formed inside of the cooling tube resulting in blockage of the cooling tube. For this reason, the reaction system was cooled down to stop progression of the reaction.

From the results shown in Example 2-1 and 2-2 and Comparative Example 2, it can be understood that by using a prescribed mixed solvents in synthesis of a borazine compound, or by feeding a solvent to a cooling section of synthesis apparatus during synthesis, formation of deposition in a cooling section is suppressed. Because of formation of deposition in a cooling section being suppressed, blockage of the cooling section can be prevented, and safe synthesis in a high yield becomes possible.

Example 3-1

Into a reactor equipped with a cooling tube, 12.1 g of lithium boron hydride as an alkali boron hydride and 187.3 g of tetraglyme as a solvent were charged with nitrogen purge, then temperature was raised to 130° C. While the reaction solution was maintained at 130° C., 40.5 g of ethylamine hydrochloride as an alkylamine salt was fed over 1 hour to proceed the reaction of the alkali boron hydride and the alkylamine salt. After that, temperature of the reaction solution was raised to 200° C., and further matured at 200° C. for 2 hours. In this reaction process, a bumping phenomenon of the reaction solution was not observed.

Example 3-2

Into a reactor equipped with a cooling tube, 33.5 g of methylamine hydrochloride as an alkylamine salt and 98.6 g of triglyme as a solvent were charged with nitrogen purge, then temperature was raised to 100° C. While the reaction solution was maintained at 100° C., a mixed liquid containing 21.0 g of sodium boron hydride as an alkali boron hydride and 88.7 g of triglyme as a solvent was fed over 1 hour to proceed the reaction of the alkali boron hydride and the alkylamine salt. After that, temperature of the reaction solution was raised to 200° C., and further matured at 200° C. for 2 hours. In this reaction process, a bumping phenomenon of the reaction solution was not observed.

Example 3-3

Into a reactor equipped with a cooling tube, 32.0 g of tetraglyme as a solvent was charged with nitrogen purge, and temperature was raised to 70° C. While the reaction solution was maintained at 70° C., a mixed liquid containing 21.0 g of sodium boron hydride as an alkali boron hydride and 88.7 g of tetraglyme as a solvent, and a mixed liquid containing 33.5 g of ethylamine hydrochloride as an alkylamine salt and 67.6 g of tetraglyme as a solvent were fed over 1 hour. After that, the reaction solution was raised to 200° C. over 2 hours, and further matured at 200° C. for 2 hours. In this reaction process, a bumping phenomenon was not observed.

Comparative Example 3-1

Into a reactor equipped with a cooling tube, 21.0 g of sodium boron hydride as an alkali boron hydride and 33.5 g of methylamine hydrochloride as an alkylamine salt were charged with nitrogen purge. Further, 187.3 g of tetraglyme as a solvent was fed. After that, the reaction solution was raised to 100° C. over 1 hour, however, since a bumping phenomenon of the reaction solution was observed, the reaction solution was cooled down to stop the reaction.

| | Synthesis process | Temperature of reaction solution | Bumping phenomenon in reaction solution |
|---|---|---|---|
| Example 3-1 | To ($AB_4H$ + solvent) $RNH_3X$ was fed | 130° C. ↓ 200° C. | No |
| Example 3-2 | To ($RNH_3X$ + solvent) ($AB_4H$ + solvent) was fed | 100° C. ↓ 200° C. | No |
| Example 3-3 | To solvent ($RNH_3X$ + solvent) and ($AB_4H$ + solvent) were fed | 70° C. ↓ 200° C. | No |
| Comparative Example 3 | To ($AB_4H$ + $RNH_3X$) solvent was fed | Reaction was stopped at 100° C. | Yes |

As described above, by the present invention, it is possible to control a reaction between an alkali boron hydride and an alkylamine salt, and an instantaneous generation of a large amount of hydrogen gas can be prevented.

Example 4

Synthesis Example

Into a 4 L reactor equipped with a condenser, 335 g of methylamine hydrochloride as an alkylamine salt and 1,000 g of triglyme as a solvent were charged with nitrogen purge, and temperature was raised to 100° C. After raising temperature, a slurry prepared by adding 210 g of sodium boron hydride as an alkali boron hydride to 1,000 g of triglyme was added over 90 min. After addition of the slurry, the reaction solution was raised to 200° C. and further matured for 2 hours to form N,N',N''-trimethylborazine (hereinafter, also referred to as "TMB"). After maturation, the condenser was removed, and a Claisen connecting tube and a Liebig cooling tube were fitted up, then N,N',N''-trimethylborazine was distilled off.

Into a 500 ml flask equipped with a Claisen connecting tube and a Liebig cooling tube, 150 g of N,N',N''-trimethylborazine obtained in the Synthesis Example was charged, then distillation was conducted under the atmospheric pressure at a distilling temperature in a range of 155 to 160° C., and a fraction at a distilling temperature of 130 to 133° C. was batched off. The distillate thus batched off was purified again by the similar atmospheric distillation.

After the distillation purification, the distillate was filtered under reduced pressure using a 0.45 μm PTFE membrane filter. The filtrate was analyzed by a gas chromatography (Shimadzu Corp., GC-14B, column: Hitachi Science Systems Ltd., UltraALLOY(8H)), to find out 0.02% by mass of boron ether compound as a component other than N,N',N"-trimethylborazine. An amount of N-alkylcycloborazane was below the detection limit.

Comparative Example 4

TMB obtained in the Synthesis Example was analyzed by a gas chromatography (Shimadzu Corp., GC-14B, column: Hitachi Science Systems Ltd., UltraALLOY(8H)), to find out 0.2% by mass of N-alkylcycloborazane and 0.2% by mass of boron ether compound as a component other than N,N',N"-trimethylborazine.

|  | Purification Process | Total content of N-alkylcycloborazane and boron ether compound |
| --- | --- | --- |
| Example 4 | Distillation purification + Filtration | 0.02% by mass |
| Comparative Example 4 | Distillation purification only | 0.4% by mass |

As shown in the table, it is understood that by applying filtration after distillation purification, impurities contained in N-alkylborazine can be effectively removed.

The present application is based on Japanese Patent Application No. 2005-028068 filed on Feb. 3, 2005, Japanese Patent Application No. 2005-030598 filed on Feb. 7, 2005, Japanese Patent Application No. 2005-151501 filed on May 24, 2005, and Japanese Patent Application No. 2005-242733 filed on Aug. 24, 2005, and the disclosures are incorporated herein by reference in entirety.

What is claimed is:

1. A method for producing a purified N-alkylborazine compound comprising:

reacting a) an alkali boron hydride represented by $ABH_4$ (A represents lithium atom, sodium atom or potassium atom) and an amine salt represented by $(RNH_3)_nX$ (R represents hydrogen atom or alkyl group, X represents sulfate group or halogen atom, and n is 1, or 2), or b) diborane ($B_2H_6$) and an amine represented by $RNH_2$ (R represents hydrogen atom or alkyl group) to obtain an N-alkylborazine compound of the following formula:

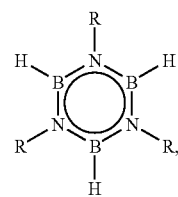

in which R is alkyl;

purifying by distillation the N-alkylborazine compound; and separating undesired compounds from the N-alkylborazine compound by filtration to obtain N-alkylborazine having a purity not lower than 99.9% by mass.

2. An N-alkylborazine composition comprising an N-alkylborazine compound, an N-alkylcycloborazane compound, and a boron ether compound, wherein the amount of the N-alkylborazine compound is not lower than 99.9% by mass and the total amount of the N-alkylcycloborazane and the boron ether compounds is not higher than 0.1% by mass.

* * * * *